United States Patent
Tahmasebi Maraghoosh et al.

(10) Patent No.: US 10,448,927 B2
(45) Date of Patent: Oct. 22, 2019

(54) SYSTEM AND METHOD FOR IDENTIFYING CANCEROUS TISSUE

(71) Applicants: KONINKLIJKE PHILIPS N.V., Eindhoven (NL); THE UNIVERSITY OF BRITISH COLUMBIA, Vancouver, British Columbia (CA)

(72) Inventors: Amir Mohammad Tahmasebi Maraghoosh, Melrose, MA (US); Purang Abolmaesumi, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/572,957

(22) PCT Filed: Jun. 1, 2016

(86) PCT No.: PCT/IB2016/053204
§ 371 (c)(1),
(2) Date: Nov. 9, 2017

(87) PCT Pub. No.: WO2016/198990
PCT Pub. Date: Dec. 15, 2016

(65) Prior Publication Data
US 2018/0103932 A1    Apr. 19, 2018

Related U.S. Application Data

(60) Provisional application No. 62/174,554, filed on Jun. 12, 2015.

(51) Int. Cl.
*A61B 8/08*    (2006.01)
*G06K 9/62*    (2006.01)
(Continued)

(52) U.S. Cl.
CPC ............ *A61B 8/5223* (2013.01); *A61B 8/085* (2013.01); *G06K 9/627* (2013.01); *G06K 9/6267* (2013.01);
(Continued)

(58) Field of Classification Search
CPC .. G06K 9/627; G06K 9/6267; G06K 2209/05; G06T 7/0016; G06T 2207/30096;
(Continued)

(56) References Cited

U.S. PATENT DOCUMENTS 6,238,342 B1 *   5/2001   Feleppa .................. A61B 8/08
                                                               600/437
8,788,019 B2   7/2014   Downey et al.
(Continued)

OTHER PUBLICATIONS

Uniyal, N. et al., "Ultrasound-based approaches to tissue classification for breast and prostate cancer diagnosis"; Thesis for Masters Electrical and Computer Engineering, University of British Columbia, Aug. 2014.
(Continued)

*Primary Examiner* — Jon Chang

(57) ABSTRACT

A system and method for identifying a characteristic of a region of a subject, such as whether a region is cancerous, which includes an ultrasonic imaging device that acquires a first and second set of time series data from a region of a subject during a first and second time period. The system includes a comparison device (120) that receives first and second sets of time series data (116, 118) and computes differential data (119) therebetween at one or more features. A processing device (130) receives the differential data and inputs the differential data into a classifier (132) trained with reference differential data concerning the one or more features as well as an identification of the ground truth concerning the region. A determination device (136) is config-
(Continued)

ured to determine whether the region contains the characteristic based on an output from the classifier.

19 Claims, 4 Drawing Sheets

(51) Int. Cl.
*G16H 50/20* (2018.01)
*G06T 7/00* (2017.01)
*G16H 30/40* (2018.01)
*G16H 50/30* (2018.01)
*G16H 50/70* (2018.01)

(52) U.S. Cl.
CPC .......... *G06T 7/0016* (2013.01); *G16H 30/40* (2018.01); *G16H 50/20* (2018.01); *G16H 50/30* (2018.01); *G16H 50/70* (2018.01); *G06K 2209/05* (2013.01); *G06T 2207/10016* (2013.01); *G06T 2207/10132* (2013.01); *G06T 2207/20081* (2013.01); *G06T 2207/20224* (2013.01); *G06T 2207/30081* (2013.01); *G06T 2207/30096* (2013.01)

(58) Field of Classification Search
CPC . G06T 2207/20224; G06T 2207/30081; G06T 2207/10016; G06T 2207/10132; G06T 2207/20081; A61B 8/5223; A61B 8/085; G16H 50/70; G16H 30/40; G16H 50/30; G16H 50/20
See application file for complete search history.

(56) References Cited

U.S. PATENT DOCUMENTS

| | | |
|---|---|---|
| 2006/0110018 A1 | 5/2006 | Chen et al. |
| 2010/0063393 A1 | 3/2010 | Moradi et al. |
| 2011/0274330 A1 | 11/2011 | Mori et al. |
| 2015/0196281 A1* | 7/2015 | Takagi ................ A61B 8/06 600/408 |
| 2016/0098621 A1 | 4/2016 | Maraghoosh et al. |

OTHER PUBLICATIONS

Volkin, D. et al., "Multiparametric magnetic resonance imaging (MRI) and subsequent MRI/ultrasonography fusion-guided biopsy increase the detection of anteriorly located prostate cancers"; BUI Int 2014; 114:E43-E49.

Moradi, M. et al., "Ultrasound RF time series for tissue typing: First in vivo clinical results". Medical Imaging 2013, Computer Aided Diagnosis. Proc SPIE 8670, 2013.

Uniyal, N. et al., "Ultrasound RF time series for classification of breast lesions", IEEE Trans Med Imaging, vol. 34, No. 2, Feb. 2015, pp. 652-661.

Muller, B.G. et al., "Imaging modalities in focal therapy: patient selection, treatment guidance, and follow-up". Curr Opin Urol. May 2014; 24(3):218-24.

Imani, F. et al, "Augmenting MRI-Transrectal Ultrasound-Guided Prostate Biopsy with temporal Ultrasound Data: A Clinical Feasibility Study". International Journal of Computer Assisted Radiology and Surgery, Jun. 2015, vol. 10, Issue 6, pp. 727-735.

\* cited by examiner

SYSTEM AND METHOD FOR IDENTIFYING CANCEROUS TISSUE

CROSS-REFERENCE TO PRIOR APPLICATIONS

This application is the U.S. National Phase application under 35 U.S.C. § 371 of International Application Serial No. PCT/IB2016/053204, filed on Jun. 1, 2016, which claims the benefit of U.S. Application Ser. No. 62/174,554, filed on Jun. 12, 2015. This application is hereby incorporated by reference herein.

BACKGROUND

Technical Field

This disclosure relates to diagnostic systems and methods and, in particular, systems and methods for identifying cancerous tissue and methods for diagnostic treatment.

Description of the Related Art

Numerous diagnostic procedures have been developed to identify cancerous tissue. With respect to prostate cancer, the most popular diagnostic procedures include a test for the biomarker prostate-specific antigen (PSA) and a digital rectal examination. If the results of these diagnostic procedures are indicative of potential prostate cancer, then a biopsy is performed to confirm the presence of the cancerous tissue. Unfortunately, PSA has a low specificity which can generate a high level of false positives. Due to the increasing use of PSA tests, there has been a steady rise in the diagnosis of prostate cancer with rates of over-diagnosis estimated to be as high as 50%.

Overtreatment due to the low specificity of PSA measurements and/or low-predictive value of known diagnostic imaging techniques leads to unnecessary treatment procedures along with the possible complications associated with such procedures. Overtreatment imposes a significant health toll on men who experience side-effects from the treatment.

Recently, there has been significant interest in using multi-parametric Magnetic Resonance Imaging (mpMRI) for diagnosis of prostate cancer. mpMRI provides a combination of several magnetic resonance imaging (MM) tests such as dynamic contrast enhanced MRI, proton magnetic resonance spectroscopic imaging and diffusion-weighted MRI. Proton magnetic resonance spectroscopic imaging provides metabolic information. Diffusion-weighted MRI displays the Brownian motion of extracellular water molecules. Dynamic contrast enhanced MRI visualizes tissue vascularity. The combination of anatomic, biologic, metabolic, and functional dynamic information offered by mpMRI has been shown to improve prostate cancer detection accuracy. More specifically, it has been shown that the accuracy, sensitivity, and positive predictive value of prostate cancer detection using mpMRI for tumor foci greater than 1.0 cm in diameter are 79.8%, 85.3%, and 92.6%, respectively. However, the accuracy, sensitivity and positive predictive value of prostate cancer detection using mpMRI drop to 24.2%, 26.2%, and 75.9% for tumor foci smaller than 1.0 cm.

Under traditional diagnostic methods, if the patient exhibits a rising PSA despite negative biopsy results, the patient is sent back for re-biopsy. While multi-parametric MRI is useful in identifying regions that are suspected to be cancer, the resolution is low and no definite diagnosis can be made, especially for smaller tumors. Additionally, multi-parametric MRI is very expensive and the workflow of the procedure is quite complex. Therefore, an additional mpMRI for re-biopsy cases imposes quite significant costs and may provide inaccurate results.

Ultrasound-based imaging of cancer is well known in the art. For example, MM transrectal ultrasound guided targeted biopsy is often used to identify cancerous tissues in the prostate. While conventional B-mode ultrasound has been utilized to visualize tumors, this type of ultrasound is not very reliable for all types of tumors because the echogenecity of numerous tumors are similar to that of surrounding normal tissue and are difficult to discern on B-mode images. Recent studies have demonstrated that the utilization of radio frequency (RF) ultrasound time-series data for prostate cancer detection may exhibit improvements over B-mode ultrasound.

SUMMARY

In accordance with the present principles, a system for identifying cancerous regions in a subject includes an ultrasonic imaging device. The ultrasonic imaging device is configured to acquire a first set of time series data from a region of a subject during a first temporal period and a second set of time series data during a second temporal period. The system also includes a comparison device that is configured to receive first and second sets of time series data and compute differential data between the first and second sets of time series data at one or more features. A processing device is configured to receive the differential data and input the differential data into a classifier trained with reference differential data concerning the one or more features obtained from the same region in a plurality of reference subjects. The reference differential data further includes an identification of whether a tissue type is cancerous or benign based on a histopathology of the tissue. A determination device is configured to determine whether the region is cancerous based on an output from the classifier.

In another embodiment, a system for identifying cancerous regions in a subject includes a workstation. The workstation includes one or more processors, memory and an interface. An imaging device is configured to acquire a first set of time series data from a region of a subject during a first temporal period and a second set of time series data during a second temporal period. The workstation further includes a comparison module configured to receive the first and second sets of time series data and compute differential data between the first and second sets of time series data at one or more features. A processing module is configured to receive the differential data and input the differential data into a classifier trained with reference differential data concerning the one or more features obtained from the same region in a plurality of reference subjects. The reference differential data further includes an identification of whether a tissue type is cancerous or benign based on a histopathology of the tissue. A determination device is configured to determine whether the region is cancerous based on an output from the classifier.

In another embodiment, a method for identifying characteristics of a region of a subject includes the steps of acquiring a first set of time series data from a region of a subject during a first temporal period and acquiring a second set of time series data from the ultrasonic imaging device during a second temporal period. Differential data between the first and second sets of time series data is computed at one or more features. The differential data is input into a classifier trained with reference differential data concerning the one or more features obtained from the same region in a plurality of reference subjects. The reference differential data further includes a ground truth concerning the characteristics of the region. A characteristic of the region is determined based on an output from the classifier. These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
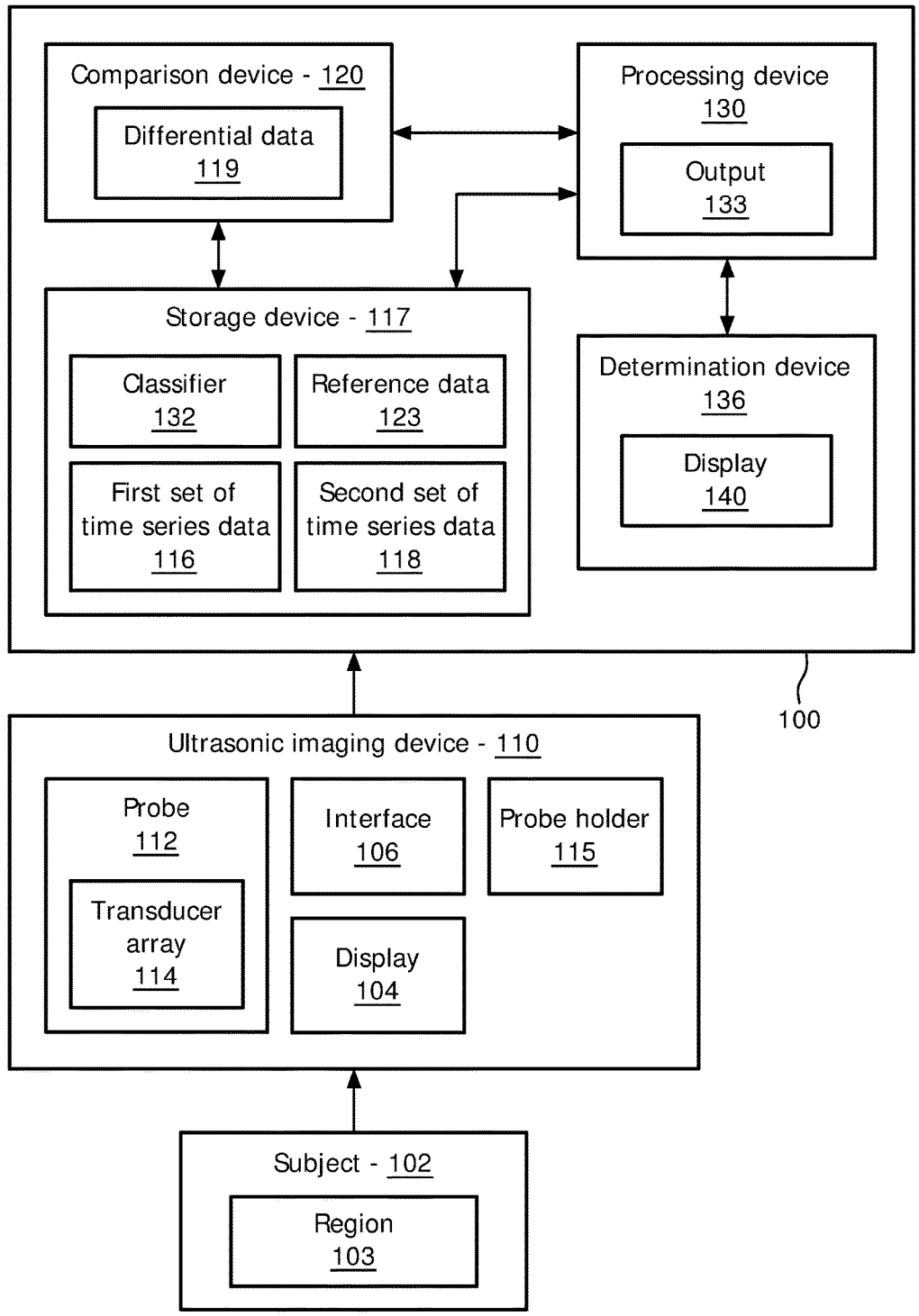
FIG. 1 is a block/flow diagram showing a system for identifying cancerous tissue in accordance with one illustrative embodiment.

In accordance with the present principles, a system for identifying cancerous regions in a subject is provided which utilizes differential data from time series data acquired from the subject and a classifier which includes reference differential data and ground truths based on histopathology. The system includes an ultrasonic imaging device that is configured to acquire a first set of time series data from a region of a subject during a first temporal period and a second set of time series data during a second temporal period. The system also includes a comparison device that is configured to receive first and second sets of time series data and compute differential data between the first and second sets of time series data at one or more features.

A processing device is configured to receive the differential data and input the differential data into a classifier trained with reference differential data concerning the one or more features obtained from the same region in a plurality of reference subjects. The reference differential data further includes an identification of whether a tissue type is cancerous or benign based on a histopathology of the tissue. A determination device is configured to determine whether the region is cancerous based on an output from the classifier.

The system provides improved detection of cancerous tissue or tumors and is cost effective with a less complex workflow as compared to mpMRI. The system augments a diagnosis provided by a first targeted biopsy and may obviate the need for an additional mpMRI for re-biopsy cases.

It should be understood that the present invention will be described in terms of medical diagnostic systems. However, the teachings of the present invention are much broader and in some embodiments, the present principles are employed in quantitatively evaluating complex biological or mechanical systems. Furthermore, while the invention may be described specifically in relation to detection of prostate cancer, the present principles are applicable to internal evaluation procedures of biological systems in all areas of the body such as the lungs, liver, brain, uterus, gastrointestinal tract, excretory organs, blood vessels, and any other solid organ tissue, tumor tissue and homogenously or heterogeneously enhancing structures of the body. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Similarly, it will be appreciated that various processes may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

In accordance with the present principles, a system for identifying cancerous regions in a subject is provided. Referring now to the drawings in which like numerals represent the same or similar elements and initially to FIG. 1, a system 100 includes an ultrasonic imaging device 110 which features a transducer device or probe 112 having a transducer array 114 for transmitting ultrasonic waves and receiving echo information. The transducer array 114, for example, can include a two dimensional array of transducer elements capable of scanning in both elevation and azimuth dimensions for 2D and/or 3D imaging. The ultrasonic imaging device 110 is preferably a radio frequency ("RF") ultrasonic imaging device. The ultrasonic imaging device 110 may include a non-handheld probe holder 115 or the probe 112 may be configured for being handheld.

The ultrasonic imaging device 110 may further include a display 104 for viewing internal images of a subject (patient) 102 or volume. The ultrasonic imaging device 110 may further include an interface 106 to permit a user to interact with the device 100 and its components and functions. The interface 106 may include a keyboard, mouse, a joystick, a haptic device, or any other peripheral or control to permit user feedback from and interaction with the device 110.

The ultrasonic imaging device 110 is configured to acquire time series data which is a temporal sequence of ultrasound data. More specifically, the temporal period concerns the time for acquisition of successive ultrasound data frames. This time period is normally reflective of the frame rate of the ultrasonic imaging device and is typically in the order of 10 s of Hz. For example, the time series data may comprise a few hundred frames and may be acquired over the course of several seconds to several minutes of scanning by the ultrasonic imaging device 110. The time series data acquisition is taken from a "steady state" wherein the ultrasonic device remains fixed at the same location. Techniques such as breath-hold techniques or registration techniques may be implemented to compensate for motion during the acquisition when the ultrasound imaging is performed on a subject 102.

The ultrasonic imaging device 110 is configured to acquire a first set 116 of time series data from a specific region(s) 103 of the subject 102 at a first time period. The ultrasonic imaging device 110 is also configured to acquire a second set 118 of time series data from the same region of the subject 102 at a second time period. For example, the first set 116 of time series data may be acquired during the time that an initial biopsy procedure is performed on the subject 102 by their medical practitioner and the second set 118 of time series data may be acquired at a follow-up diagnostic session.

The system 100 further includes a comparison device 120. The comparison device 120 is configured to receive the first 116 and second 118 sets of time series data. The time series data may be stored in a storage device 117 such as a database or other storage devices known in the art. The comparison device 120 is configured to compare the first 116 and second 118 sets of time series data at one or more features.

Furthermore, the comparison device 120 is configured to compute differential data 119 between the first 116 and second 118 sets of time series data. For example, when the ultrasonic imaging device 110 comprises an RF ultrasound, the differential data 119 may be the differences between the two RF signals at one or more features. Alternatively, the differential data 119 may be a variety of derivative values concerning the differences.

The determination of differential data provides a highly sensitive measurement between the first and second sets of time series data that is calibrated for each patient. Since the acquisition of the differential data is between two sets of ultrasound signals from the same patient, the differences in the ultrasound data are directly indicative of a change in tissue characteristics. This provides improved accuracy concerning tissue identification as compared to using reference time series data to analyze the time series data from the subject where it is necessarily assumed that the subject has similar mean ultrasound data characteristics as the reference subjects. This analysis may be inaccurate for a patient that displays uncharacteristic ultrasound data for certain tissue as compared to the reference subjects.

The system 100 further includes a processing device 130 which is configured to receive the differential data 119 from the storage device 117 or otherwise. The processing device 130 utilizes a supervised machine learning classifier 132 that is trained with reference differential data 123 concerning the one or more features obtained from the same region in a plurality of reference subjects. More specifically, two sets of time series data are acquired from a plurality of reference subjects from the same regions of the reference subjects as the regions 103 that the time series data is acquired from the subject 102. The two sets of time series data are acquired at different time points, such as during the time that at an initial biopsy procedure is performed and at a follow-up diagnostic session. The differences between the first and second sets of time series data from the reference subjects is determined in order to provide reference differential data 123 which is input into the training database.

The reference data also includes the ground truth regarding the tissue type, e.g., a classification of whether the tissue type is cancerous or benign. The ground truth will be determined by the histopathology for that tissue. The classifier 132 and the reference data 123 may be included in the storage device 117 as shown in FIG. 1 or may be included in other components of the system.

The features are preferably spectral features or wavelet features which are extracted from the reference differential data 123, such as the differences in RF signals. The spectral features represent the signature of backscattered signal from the tissue. A machine learning and classification framework is used to build the classifier 132 which is trained to correlate the features to the result of histopathology analysis in order to separate and interpret different features from different tissue regions according to the reference differential data 123. The classifier 132 includes a sufficient number of time-series data with a variety of tissue types (e.g., both benign and malignant) and with different cancer grading to provide an accurate classification. In one embodiment, the ground truth may comprise a cancer grading that is based on e.g., a Gleason score. The classifier 132 is configured to generate an output 133 based on the results of the differential data 119 of the subject input into the classifier.

A determination device 136 is configured to grade the tissue based on the classifier output 133 and determine whether the region 103 of the subject 102 is cancerous based on the classifier output. In one embodiment, the determination device 136 is configured to generate a determination as to whether re-biopsy or active surveillance is needed for the subject based on the output from the classifier. The determination device 136 may be configured to generate the determination on a display 140. However, the determination device may be configured to generate the determination by an audio signal or other means known in the art.

The system which utilizes differential data 119 from the time series data of the subject and a classifier 132 which includes reference differential data 123 and ground truths based on histopathology has been shown to provide improved detection of cancerous tissue/tumors and is cost effective and has a simpler workflow as compared to mpMRI. Furthermore, the system extracts the features from the first and second sets of time series data prior to performing the tissue identification analysis. The differential comparison of these features, such as comparing the feature histograms to identify the change in feature distributions, provides a clearer and more precise identification of tissue than if the features were used directly and independently during the tissue identification analysis in a machine classifier that is trained by the reference data.

Differential ultrasound features may be combined with features from mpMRI or features from differential mpMRI for improved detection."

While the systems are generally described in discrete parts in FIG. 1, the systems and their components may be incorporated into a single system such as the Philips® UroNav™ system that is operated in an ultrasound-only workflow.

Figure 2:
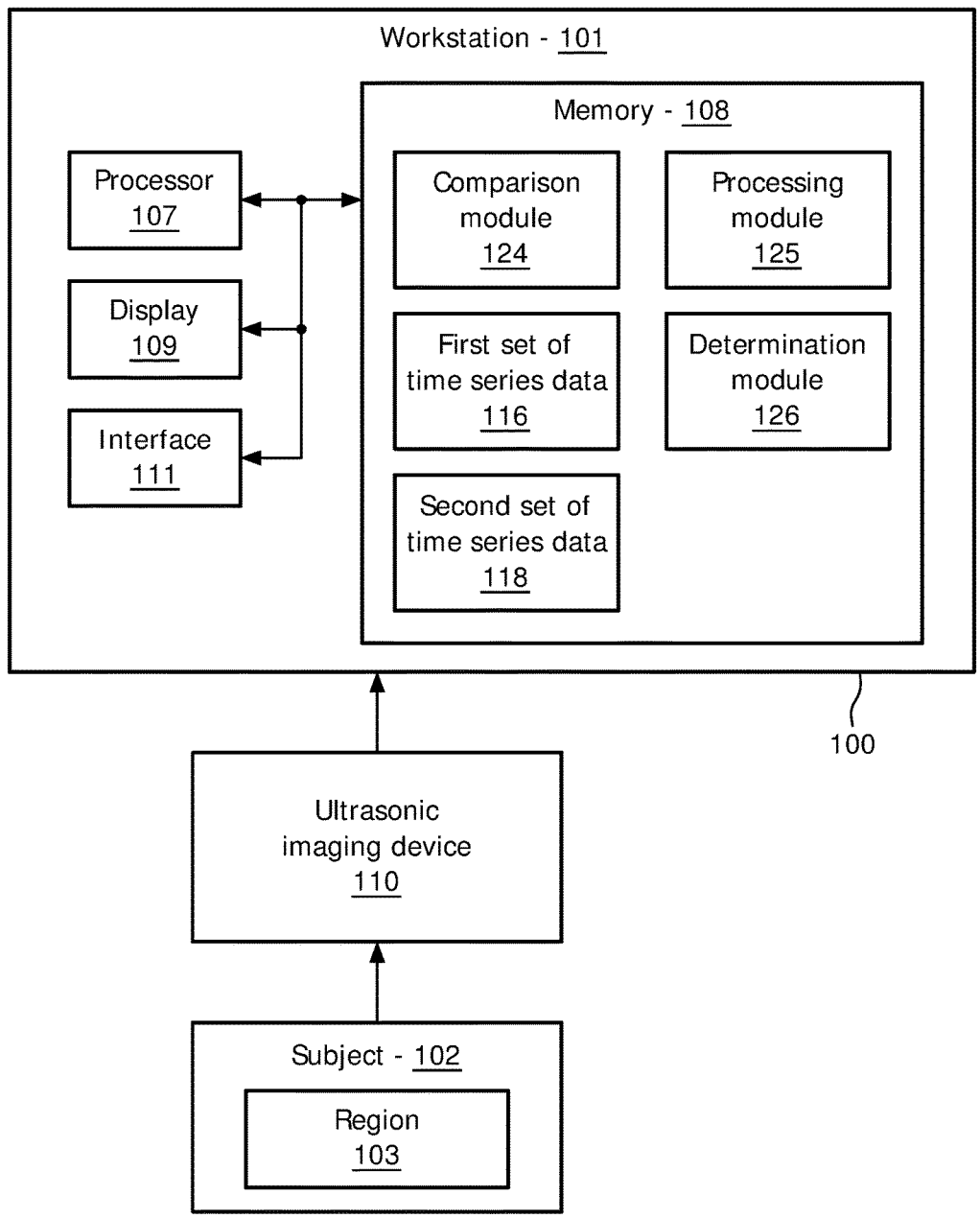
FIG. 2 is a block/flow diagram showing a system for identifying cancerous tissue in accordance with a second illustrative embodiment.

As shown in FIG. 2, in one embodiment, the system 100 may include a workstation 101 from which the procedure is supervised and/or managed. The workstation 101 preferably includes one or more processors 107, memory 108 for storing programs and applications and a display 109 which permits a user to view images and interact with the workstation 101. The system 100 may further include an interface 111 which may feature a keyboard, mouse, a joystick, a haptic device, or any other peripheral or control to permit user feedback from and interaction with the workstation 101.

The workstation 101 may include a comparison module 124 which is configured to receive the first and second sets of time series data 116, 118 acquired by the imaging device 110 and compute differential data between the first and second sets of time series data at one or more features. The comparison module 124 provides the same functionality as the comparison device 120 previously described in the embodiment shown in FIG. 1.

The workstation 101 may also include an integrated processing module 125 which is configured to receive the differential data 119 and input the differential data into an integrated classifier trained with reference differential data concerning the one or more features obtained from the same region in a plurality of reference subjects. The reference differential data further includes an identification of whether a tissue type is cancerous or benign based on a histopathology of the tissue. The processing module 125 provides the same functionality as the processing device 130 previously described in the embodiment shown in FIG. 1.

The workstation 101 may also include an integrated determination module 126 which is configured to determine whether the region is cancerous based on an output from the classifier of the processing module 125. The determination module 126 provides the same functionality as the determination device 136 previously described in the embodiment shown in FIG. 1.

Figure 3:
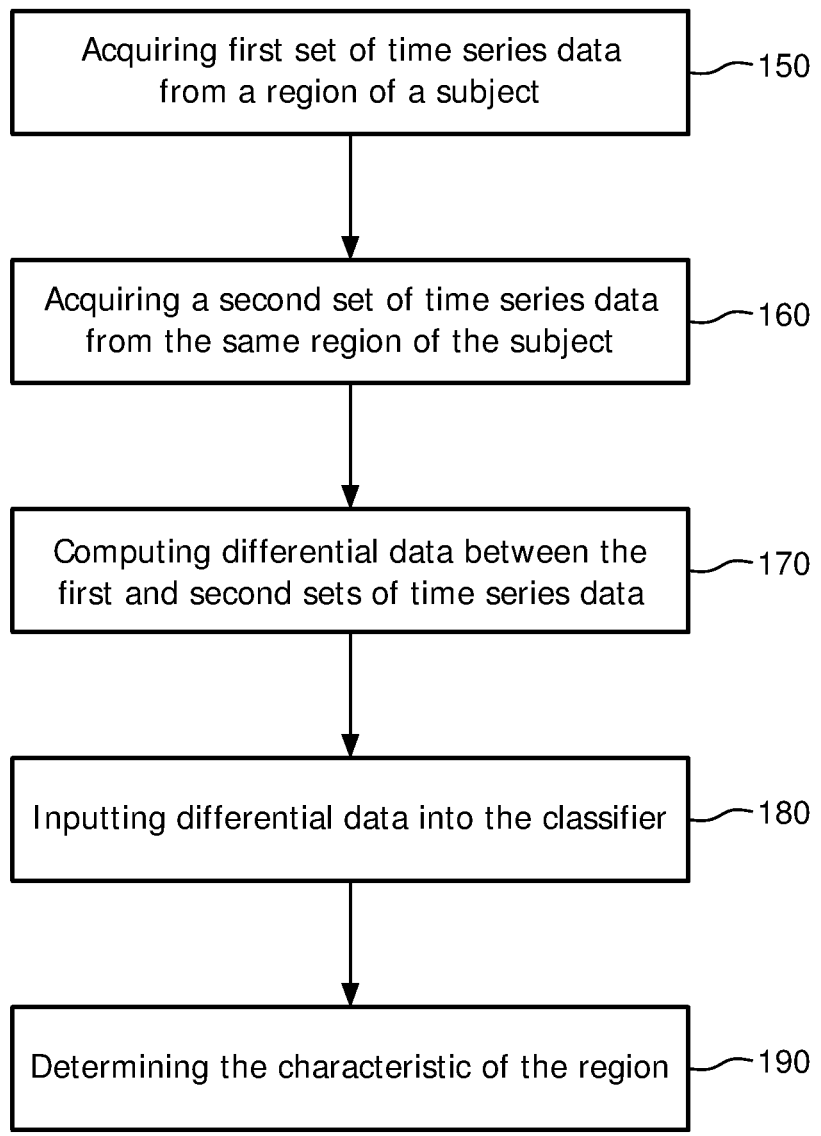
FIG. 3 is a flow diagram showing a method for identification of cancerous tissue.

Referring to FIG. 3, methods 144 for identifying characteristics of a region of a subject, such as whether a region of tissue is cancerous are illustratively shown in accordance with the present principles. In block 150, a first set of time series data is acquired from a region of a subject during a first time period. The first set of time series data is preferably acquired from the subject by using an ultrasonic imaging device. The ultrasonic imaging device is preferably an RF frequency ultrasonic imaging device. The data is acquired from a "steady state", as previously described.

In block 160, a second set of time series data is acquired from the same region of the subject at a second time period. For example, the step 150 of acquiring a first set of time series data may be performed at the time of an initial biopsy procedure and the step 160 of acquiring the second set of time series data may be performed at a follow-up diagnostic session.

In block 170, differential data between the first and second sets of time series data is computed at one or more features. For example, when the first and second sets of time series data are acquired by an RF ultrasound device, the step 170 of computing differential data may be performed by obtaining the differences between the RF signals of the first and second sets of time series data at one or more features.

Once the differential data is computed 170, the differential data is input 180 into a supervised machine learning classifier that is trained with reference differential data concerning one or more features obtained from the same region as the first and second sets of time series data in a plurality of reference subjects. The classifier is also trained with the ground truth concerning the characteristics of the region. For example, when the characteristic to be identified is the presence of cancerous tissue, the ground truth may be whether the tissue is benign or cancerous as determined by the histopathology for that tissue. The classifier correlates the differential data with the result of histopathology analysis and generates an output based on the results of the differential data of the subject input into the classifier.

In block 190, the step of determining the characteristic of the region, such as whether the region contains cancerous tissue, is performed based on an output from the classifier. The step of determining whether the region contains cancerous tissue may include a graded score concerning the tissue. The determination may further comprise a recommendation concerning whether re-biopsy or active surveillance of the subject should be performed.

Figure 4:
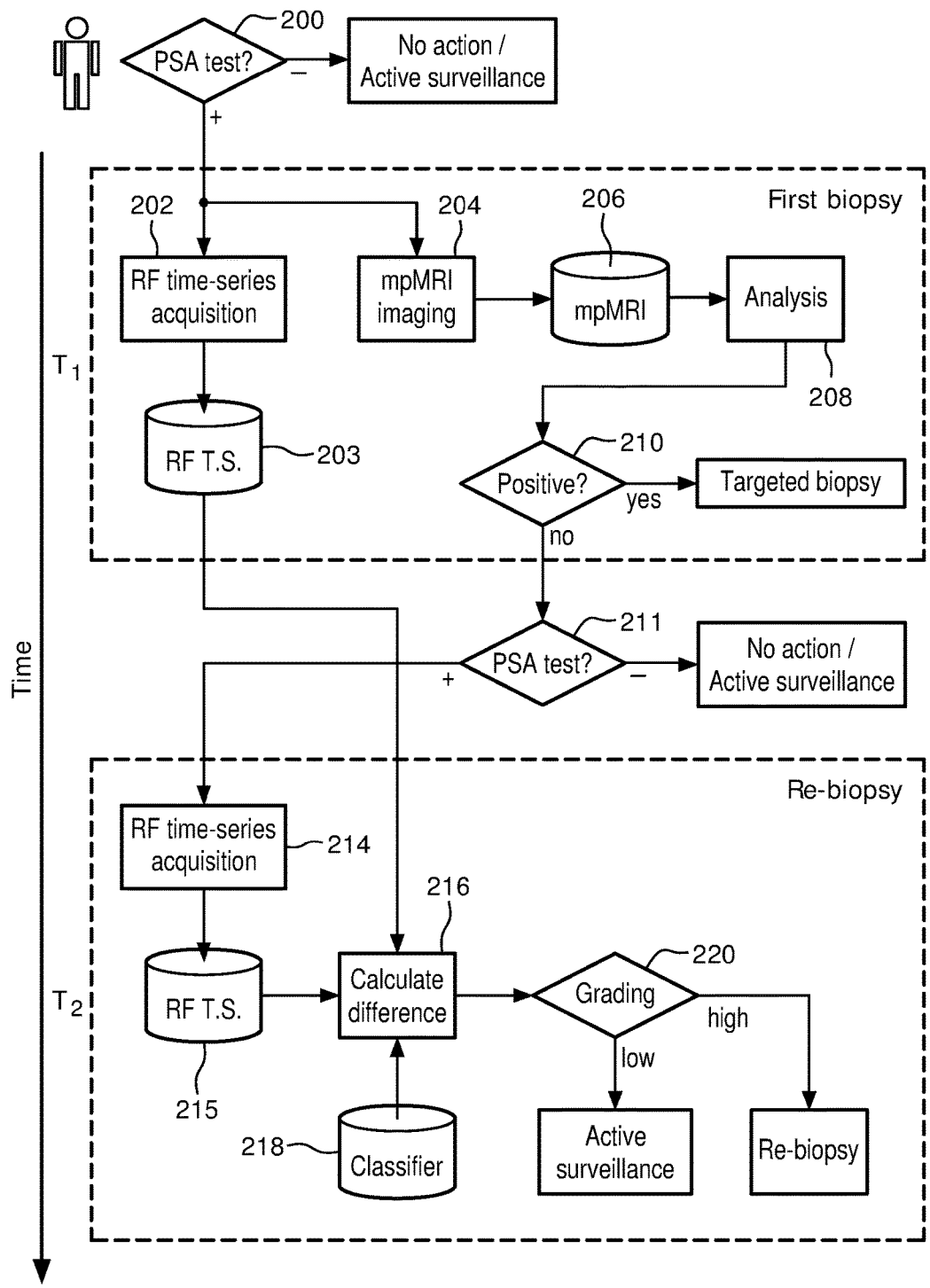
FIG. 4 is a flow diagram showing a method for diagnostic treatment of a subject.

Referring to FIG. 4, methods for performing diagnostic treatment of a subject are illustratively shown in accordance with the present principles. In block 200, a PSA test is performed on the subject. If the PSA test indicates decreasing PSA levels in the subject, active surveillance may be taken of the subject. Alternatively, no action may be taken on the subject if the PSA test reveals decreasing PSA levels. In contrast, if the PSA test indicates that the subject's PSA levels are rising, then a first set of time series data is acquired 202 from the subject and mpMRI imaging of the subject is performed 204 on the specific region of the subject. As previously discussed, the first set of time series data may be acquired by a steady state, RF ultrasonic imaging device or by other devices known in the art. The first set of time series data may be transferred 203 into a database or other storage device known in the art.

The mpMRI data may be transferred 206 to a database or other storage device known in the art. The mpMRI data is then analyzed 208 to determine whether the tissue is indicative of cancer. If the results of the mpMRI analysis are indicative of cancer 210, a targeted biopsy is performed on the subject to confirm whether cancerous tissue/tumor is present. For example, an MRI-transrectal ultrasound-guided targeted biopsy may be performed on the subject. If the results of the mpMRI analysis are negative or if the targeted biopsy does not reveal cancer then another PSA test is administered 211 on the patient.

If the results of the second PSA test indicate decreasing PSA levels, then active surveillance of the patient is taken. Alternatively, no further diagnostic action may be taken on the subject if the second PSA test indicates decreasing PSA levels. If the results of the second PSA test indicates rising PSA levels, a second set of time series data is acquired 214 from the same region of the subject during a second time period. The second set of time series data may be transferred 215 to a database or other storage device known in the art.

Differential data between the first and second sets of time series data is then computed 216 at one or more features. For example, when the first and second sets of time series data are acquired by an RF ultrasound, the differential data may be performed by obtaining the differences between the RF signals of the first and second sets of time series data at one or more features.

Once the differential data is computed, the differential data is input 218 into a supervised machine learning classifier that is trained with reference differential data and the ground truth regarding the tissue type as determined by the histopathology for that tissue, as previously described. The classifier correlates the differential data with the result of histopathology analysis.

The classifier generates an output based on the results of the differential data of the subject input into the classifier. Based on the output, a determination is rendered 220 concerning whether the region is cancerous. The determination may be made on a graded scale. A high grading indicates that a re-biopsy should be performed. A low grading indicates that active surveillance may be performed.

This method for performing diagnostic treatment of a subject uses differentials of time series data to augment a first targeted biopsy, such as an MRI-transrectal ultrasound-guided targeted biopsy. The method obviates the need for an additional mpMRI for re-biopsy cases.

It is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments the method and device for identifying cancerous regions in a subject (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims.

Having thus described the details and particularity required by the patent laws, what is claimed and desired protected by Letters Patent is set forth in the appended claims:

1. A system for identifying cancerous regions in a subject, comprising:
    an ultrasonic imaging device configured to acquire a first set of time series data from a region of a subject during a first temporal period and a second set of time series data during a second temporal period wherein the first temporal period is at a time of an initial biopsy procedure and the second temporal period is at a time of a follow-up diagnostic session;
    a comparison device configured to receive the first and second sets of time series data and compute differential data between the first and second sets of time series data at one or more features, wherein the differential data are directly indicative of a change in tissue characteristics between the time of the initial biopsy procedure and the time of the follow-up diagnostic session;
    a processing device configured to receive the differential data and input the differential data into a classifier trained with reference differential data concerning the one or more features obtained from the same region in a plurality of reference subjects, said reference differential data further including an identification of whether a tissue type is cancerous or benign based on a histopathology of the tissue; and
    a determination device configured to determine whether the region is cancerous based on an output from the classifier.

2. The system as recited in claim 1, wherein the ultrasonic imaging device comprises a radio frequency ultrasonic imaging device.

3. The system as recited in claim 1, wherein the ultrasonic imaging device is configured to acquire the first and second set of time series data at a fixed position.

4. The system as recited in claim 1, wherein the ultrasonic imaging device is configured to acquire the first and second set of time series data over the course of several seconds to several minutes of scanning.

5. The system as recited in claim 1, further comprising a storage device configured to receive and store the first and second sets of time series data.

6. The system as recited in claim 2, wherein the differential data that the comparison device is configured to compute comprises the differences between the RF signals of the first and second sets of time series data at one or more features.

7. The system as recited in claim 1, wherein the features comprise spectral features or wavelet features.

8. The system as recited in claim 7, wherein the features are extracted from the reference differential data.

9. The system as recited in claim 1, wherein the determination device is configured to generate a determination concerning whether re-biopsy or active surveillance is needed for the subject.

10. A system for identifying cancerous regions in a subject, comprising:
    an imaging device configured to acquire a first set of time series data from a region of a subject during a first temporal period and a second set of time series data during a second temporal period; and
    a workstation including:
      one or more processors, memory and an interface;
      a comparison module configured to:
        receive a first set of time series data acquired at an initial time period of a first session, and a second sets of time series data acquired at a follow-up time period of a second session later than the initial time period; and
        compute differential data between the first and second sets of time series data at one or more features, wherein the differential data are directly indicative of a change in tissue characteristics;
      a processing module configured to receive the differential data and input the differential data into a classifier trained with reference differential data concerning the one or more features obtained from the same region in a plurality of reference subjects, said reference differential data further including an identification of whether a tissue type is cancerous or benign based on a histopathology of the tissue; and
      a determination module configured to determine whether the region is cancerous based on an output from the classifier.

11. The system as recited in claim 10, wherein the imaging device comprises a radio frequency ultrasonic imaging device.

12. The system as recited in claim 10, wherein the imaging device is configured to acquire the first and second set of time series data at a fixed position.

13. The system as recited in claim 11, wherein the differential data that the comparison module is configured to compute comprises the differences between the RF signals of the first and second sets of time series data at one or more features.

14. The system as recited in claim 11, wherein the features comprise spectral features or wavelet features that are extracted from the reference differential data.

15. A method for identifying characteristics of a region of a subject, comprising:
   acquiring a first set of time series data from an ultrasonic imaging device from a region of a subject during a first temporal period at a time of a first imaging session;
   acquiring a second set of time series data from the ultrasonic imaging device during a second temporal period at a time of a follow-up second imaging session wherein the time of the follow-up second imaging session is later than the time of the first imaging session;
   computing differential data between the first and second sets of time series data at one or more features, wherein the differential data are directly indicative of a change in tissue characteristics between the time of the first imaging session and the time of the follow-up second imaging session;
   inputting the differential data into a classifier trained with reference differential data concerning the one or more features obtained from the same region in a plurality of reference subjects, said reference differential data further including an identification of whether a tissue type is cancerous or benign based on a histopathology of the tissue; and
   determining whether the region is cancerous based on an output from the classifier.

16. The method as recited in claim 15, wherein the first and second sets of time series data comprises radio frequency ultrasonic imaging data.

17. The method as recited in claim 16, wherein the radio frequency ultrasonic imaging data is acquired at a fixed position.

18. The method as recited in claim 15, comprising the further step of determining a cancer grading based on the output from the classifier.

19. The method as recited in claim 15, comprising the further step of determining whether a re-biopsy or active surveillance of the subject should be performed.

* * * * *